US012571797B2

(12) United States Patent
Wert et al.

(10) Patent No.: US 12,571,797 B2
(45) Date of Patent: Mar. 10, 2026

(54) LIQUID CHROMATOGRAPHY ASSAY FOR DETERMINING AAV CAPSID RATIO

(71) Applicant: Regeneron Pharmaceuticals, Inc., Tarrytown, NY (US)

(72) Inventors: Jonathan Wert, Yorktown Heights, NY (US); Li Zhi, Tarrytown, NY (US); Dingjiang Liu, Pleasantville, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 808 days.

(21) Appl. No.: 17/862,254

(22) Filed: Jul. 11, 2022

(65) Prior Publication Data

US 2023/0020428 A1    Jan. 19, 2023

Related U.S. Application Data

(60) Provisional application No. 63/359,554, filed on Jul. 8, 2022, provisional application No. 63/359,557, filed on Jul. 8, 2022, provisional application No. 63/275,138, filed on Nov. 3, 2021, provisional application No. 63/220,651, filed on Jul. 12, 2021.

(51) Int. Cl.
| | |
|---|---|
| *G01N 33/569* | (2006.01) |
| *G01N 30/34* | (2006.01) |
| *G01N 30/72* | (2006.01) |
| *G01N 30/74* | (2006.01) |
| *G01N 30/86* | (2006.01) |
| *G01N 30/96* | (2006.01) |
| *G01N 33/53* | (2006.01) |
| *G01N 33/68* | (2006.01) |

(52) U.S. Cl.
CPC ....... *G01N 33/56983* (2013.01); *G01N 30/34* (2013.01); *G01N 30/7233* (2013.01); *G01N 30/7266* (2013.01); *G01N 30/74* (2013.01); *G01N 30/8679* (2013.01); *G01N 30/96* (2013.01); *G01N 33/5308* (2013.01); *G01N 33/6848* (2013.01); *G01N 2333/015* (2013.01); *G01N 2440/10* (2013.01); *G01N 2440/14* (2013.01)

(58) Field of Classification Search
None
See application file for complete search history.

(56) References Cited

U.S. PATENT DOCUMENTS

| | | | | |
|---|---|---|---|---|
| 2021/0009964 A1* | 1/2021 | Khatwani | ............ | B01D 15/166 |
| 2021/0041451 A1* | 2/2021 | Jin | ..................... | G01N 33/6848 |

FOREIGN PATENT DOCUMENTS

| | | | | |
|---|---|---|---|---|
| WO | WO-2018035059 A1 * | 2/2018 | .......... | C07K 14/005 |
| WO | 21/138381 A1 | 7/2021 | | |

OTHER PUBLICATIONS

Qu et al., Journal of Virological Methods, vol. 140, No. 1-2, Feb. 2, 2007, pp. 183-192 (Year: 2007).*
Mahoney et al., Journal of Biological Chemistry, vol. 255, Issue 23, 1980, pp. 11199-1120 (Year: 1980).*
Ma et al., Anal Chem. Aug. 1, 2009;81(15):6534-40 (Year: 2009).*
Liu et al., Journal of Pharmaceutical and Biomedical Analysis, vol. 189, 2020, 113481 (Year: 2020).*
Liu et al., "Characterization of Adeno-Associated Virus Capsid Proteins Using Hydrophilic Interaction Chromatography Coupled with Mass Spectrometry," Journal of Pharmaceutical and Biomedical Analysis, vol. (189): 1-8, (2020).
Lock et al., "Analysis of Particle Content of Recombinant Adeno-Associated Virus Serotype 8 Vectors by Ion-Exchange Chromatography," Human Gene Therapy Methods, Part B, vol. (23): 56-64, (2012). [DOI: 10.1089/hgtb.2011.217].
Pierson et al., "Resolving Adeno-Associated Viral Particle Diversity With Charge Detection Mass Spectrometry," Analytical Chemistry, American Chemical Society, vol. (88): 6718-6725, (2016).
Qu et al., "Separation of adeno-associated virus type 2 empty particles from genome containing vectors by anion-exchange column chromatography," ScienceDiet, Journal of Virological Methods, vol. (140): 183-192, (2007).
Wang et al., "Developing an Anion Exchange Chromatography Assay for Determining Empty and Full Capsid Contents in AAV6.2," Methods & Clinical Development, American Society of Gene & Cell Therapy, vol. (15): 257-263, (2019).
WIPO Application No. PCT/US2022/036723, PCT International Search Report and Written Opinion of the International Searching Authority mailed Oct. 18, 2022.
WIPO Application No. PCT/US2022/036728, PCT International Search Report and Written Opinion of the International Searching Authority mailed Oct. 21, 2022.
WIPO Application No. PCT/US2022/036725, PCT International Search Report and Written Opinion of the International Searching Authority mailed Oct. 26, 2022.
Worner et al., "Mass Spectrometry-Based Structural Virology," Analytical Chemistry, American Chemical Society, vol. (93): 620-640, (2021).
U.S. Appl. No. 62/220,651, filed Jul. 12, 2021, Expired.
U.S. Appl. No. 63/275,138, filed Nov. 3, 2021, Expired.
U.S. Appl. No. 63/359,554, filed Jul. 8, 2022, Pending.
U.S. Appl. No. 17/862,240, filed Jul. 11, 2022, US-2023-0016717-A1, Published.

(Continued)

*Primary Examiner* — Karl J Puttlitz

(74) *Attorney, Agent, or Firm* — Schwabe, Williamson & Wyatt PC; David Mellman

(57)    ABSTRACT

Methods for determining the relative abundance of intact adeno-associated virus (AAV) capsid components in a sample of recombinant AAV particles are disclosed. In embodiments, the methods include a system regeneration process that minimizes or eliminates the presence of ghost peaks to maximize analytical accuracy and ensure product quality and consistency.

20 Claims, No Drawings

(56)          References Cited

OTHER PUBLICATIONS

PCT/US2022/036723, Jul. 11, 2022, WO 2023/287723, Published.
U.S. Appl. No. 63/220,654, filed Jul. 12, 2021, Expired.
U.S. Appl. No. 63/352,754, filed Jun. 16, 2022, Pending.
U.S. Appl. No. 17/862,248, filed Jul. 11, 2022, US-2023-0010418-A1, Published.
PCT/US2022/036725, Jul. 11, 2022, WO 2023/287724, Published.
U.S. Appl. No. 63/359,557, filed Jul. 8, 2022, Pending.
PCT/US2022/036728, Jul. 11, 2022, WO 2023/287725, Published.

* cited by examiner

LIQUID CHROMATOGRAPHY ASSAY FOR DETERMINING AAV CAPSID RATIO

CROSS-REFERENCE TO RELATED APPLICATIONS

This application claims the benefit under 35 USC § 119(e) of US Provisional Application Nos.: 63/220,651, filed Jul. 12, 2021; 63/275,138, filed Nov. 3, 2021; 63/359,554, filed Jul. 8, 2022; and 63/359,557, filed Jul. 8, 2022, each of which is incorporated herein by reference in its entirety for all purposes.

FIELD OF THE INVENTION

The present invention relates to methods for determining the relative abundance of intact adeno-associated virus (AAV) capsid components in a sample of recombinant AAV particles comprising a heterologous nucleic acid molecule using anion exchange chromatography.

BACKGROUND

Adeno-associated virus, which is a non-enveloped, single-stranded DNA virus, has emerged as an attractive class of therapeutic agents to deliver genetic materials to host cells for gene therapy, due to its ability to transduce a wide range of species and tissue in vivo, low risk of immunotoxicity, and mild innate and adaptive immune responses. The complex nature of viral vectors such as AAV require specific analytical methods to enable robust product testing and characterization.

Independent of the manufacturing approach, one characteristic of AAV production is the formation of empty capsids, which contain no heterologous gene-of-interest (GOI). The level of empty capsids can vary widely. Although the effects of empty capsids on therapeutic outcomes are incompletely understood, the quantity of empty capsids needs to be closely monitored to ensure product quality and consistency.

Multiple methods have been described to quantify empty capsids in AAV samples, and anion exchange chromatography (AEX) has been used for purification and enrichment of full AAV particles of serotypes 1, 2 and 8 (Wang, infra). Further, the application of AEX for accurate quantification of AAV serotype 6.2 has been discussed in Wang et al., *Molecular Therapy: Methods and Clinical Development*, 15:257-263, 2019. In particular, Wang reports that the structural integrity of AAV capsids under chromatographic conditions is a prerequisite for a separation method of empty and full capsids and that the presence of 2 mM $MgCl_2$ resulted in the disappearance of broad peaks and an increase in the intensity of the peaks, but that higher concentrations of $MgCl_2$ did not provide further improvement. Wang further reports that the use of tetramethyl ammonium chloride (TMAC) in the mobile phase improved separation relative to NaCl, that separation was improved at higher pH values within a range of from 7.5 to 9.0, and that the impact of buffering agents on the resolution between empty and full capsids was small, and that bis-tris propane (BTP) produced the best separation among the agents tested.

For product quality and consistency, especially in the context of good manufacturing practice (GMP) release assays, the minimization or elimination of potential sources of analytical error is paramount. One such source of analytical error is the presence of "ghost peaks," often referred to as artifacts or pseudo peaks, which are unexpectedly observed in chromatograms. Since such ghost peaks may arise from impurities or artifacts within the liquid chromatography system, their presence may result in out-of-specification investigational requirements, or lead to inconsistent and inaccurate results that are time-consuming or unacceptable for GMP product assays.

BRIEF SUMMARY OF THE INVENTION

The present disclosure is directed to a methods for determining relative abundance of intact viral capsid components in a sample of adeno-associated virus (AAV) particles.

In one aspect, the present disclosure provides a method for determining relative abundance of intact viral capsid components in a sample of adeno-associated virus (AAV) particles comprising a heterologous nucleic acid molecule, the method comprising: (a) performing a system regeneration process on a liquid chromatography system comprising a liquid chromatography (LC) instrument and an anion exchange column (AEX column), wherein the system regeneration process comprises: (i) washing the AEX column with at least 10 column volumes (CV) of mobile phase A; (ii) washing the AEX column with at least 10 CV of purified water; (iii) washing the AEX column with at least 20 CV of a wash solution comprising from 15% to 21% v/v ethanol in purified water; and (iv) washing liquid carrying components of the LC instrument with the wash solution at a flow rate of at least 0.5 mL/min for at least 30 minutes, wherein mobile phase A comprises from 15 mM to 25 mM bis-tris-propane, and from 1 mM to 3 mM magnesium chloride in purified water at a pH of from 8 to 9, and wherein the purified water has a resistivity of about 18.2 Mohm·cm at 25° C. and less than 5 ppb total organic carbon; (b) performing a system equilibration process on the liquid chromatography system, comprising purging the wash solution from the liquid carrying components of the LC instrument and the AEX column; (c) performing a sample separation process, wherein the sample separation process comprises: (i) introducing one or more blank samples into the liquid chromatography system, and running a separation gradient of mobile phase A, mobile phase B and mobile phase C through the liquid chromatography system; (ii) introducing one or more reference standard samples into the liquid chromatography system, and running a separation gradient of mobile phase A, mobile phase B and mobile phase C through the liquid chromatography system; and (iii) introducing one or more test samples of the AAV particles into the liquid chromatography system, wherein the one or more test samples comprises intact empty AAV capsids and intact full AAV capsids in a sample solution, and running a separation gradient of mobile phase A, mobile phase B and mobile phase C through the liquid chromatography system to separate the intact empty AAV capsids from the intact full AAV capsids, wherein mobile phase B comprises 15 mM to 25 mM bis-tris-propane, from 250 mM to 1 M tetramethylammonium chloride (TMAC), and from 1 mM to 3 mM magnesium chloride in purified water at a pH of from 8 to 9, and mobile phase C comprises 1.5 M to 2.5 M sodium chloride in purified water; and (d) identifying an amount of the intact empty AAV capsids and an amount of the intact full AAV capsids in each of the one or more test samples to determine the relative abundance of the intact viral capsid components in the sample of AAV particles.

In one aspect, the present disclosure provides a method for determining relative abundance of intact viral capsid components in a sample of AAV particles comprising a heterologous nucleic acid molecule, the method comprising:

(a) performing a system regeneration process on a liquid chromatography system comprising a liquid chromatography (LC) instrument and an anion exchange column (AEX column), wherein the system regeneration process comprises: (i) washing the AEX column with at least 10 column volumes (CV) of mobile phase A; (ii) washing the AEX column with at least 10 CV of purified water; (iii) optionally reversing the orientation of the AEX column to reverse the flow within the AEX column; (iv) washing the AEX column with at least 20 CV of a wash solution comprising from 15% to 21% v/v ethanol in purified water; (v) removing the AEX column from the LC instrument; and (vi) washing liquid carrying components of the LC instrument with the wash solution at a flow rate of at least 0.5 mL/min for at least 30 minutes, wherein mobile phase A comprises from 15 mM to 25 mM bis-tris-propane, and from 1 mM to 3 mM magnesium chloride in purified water at a pH of from 8 to 9, and wherein the purified water has a resistivity of about 18.2 Mohm·cm at 25° C. and less than 5 ppb total organic carbon; (b) performing a system equilibration process on the liquid chromatography system, comprising: (i) reinstalling the AEX column into the LC instrument; and (ii) purging the wash solution from the liquid carrying components of the LC instrument and the AEX column; (c) performing a sample separation process, wherein the sample separation process comprises: (i) introducing one or more blank samples into the liquid chromatography system, and running a separation gradient of mobile phase A, mobile phase B and mobile phase C through the liquid chromatography system; (ii) introducing one or more reference standard samples into the liquid chromatography system, and running a separation gradient of mobile phase A, mobile phase B and mobile phase C through the liquid chromatography system; and (iii) introducing one or more test samples of the AAV particles into the liquid chromatography system, wherein the one or more test samples comprises intact empty AAV capsids and intact full AAV capsids in a sample solution, and running a separation gradient of mobile phase A, mobile phase B and mobile phase C through the liquid chromatography system to separate the intact empty AAV capsids from the intact full AAV capsids, wherein mobile phase B comprises 15 mM to 25 mM bis-tris-propane, from 250 mM to 1 M tetramethylammonium chloride (TMAC), and from 1 mM to 3 mM magnesium chloride in purified water at a pH of from 8 to 9, and mobile phase C comprises 1.5 M to 2.5 M sodium chloride in purified water; and (d) identifying an amount of the intact empty AAV capsids and an amount of the intact full AAV capsids in each of the one or more test samples to determine the relative abundance of the intact viral capsid components in the sample of AAV particles.

In some cases, the wash solution comprises from 18%±1% v/v ethanol in purified water.

In any of the various embodiments of the methods discussed above or herein, the sample solution comprises from 1 mM to 100 mM sodium chloride. In some cases, the sample solution comprises from 60 mM to 100 mM sodium chloride.

In any of the various embodiments of the methods discussed above or herein, the sample solution comprises from 0.003% w/v to 0.007% w/v surfactant. In some cases, the sample solution comprises 0.005% w/v±0.001% w/v surfactant. In some embodiments, the surfactant is poloxamer 188.

In some embodiments, the system equilibration process comprises: (i) purging the wash solution from the liquid carrying components of the LC instrument and the AEX column with purified water at a flow rate of at least 0.5 mL/min for at least 10 minutes; (ii) washing the AEX column with at least 10 CV of purified water; (iii) washing the AEX column with at least 10 CV of mobile phase A; (iv) washing the AEX column with at least 20 CV of mobile phase B; and (v) washing the AEX column with at least 20 CV of mobile phase A.

In some embodiments, the system equilibration process comprises: (i) purging the wash solution from the liquid carrying components of the LC instrument with purified water at a flow rate of at least 0.5 mL/min for at least 10 minutes; (ii) reinstalling the AEX column in the LC instrument; (iii) washing the AEX column with at least 10 CV of purified water; (iv) washing the AEX column with at least 10 CV of mobile phase A; (v) washing the AEX column with at least 20 CV of mobile phase B; and (vi) washing the AEX column with at least 20 CV of mobile phase A. In some cases, performing the system equilibration process further comprises washing the liquid carrying components of the LC instrument with purified water at a flow rate of at least 0.5 mL/min for at least 10 minutes prior to reinstalling the AEX column into the LC instrument. In some cases, purging the wash solution from the liquid carrying components of the LC instrument with purified water is performed at a flow rate of at least 0.5 mL/min for at least 30 minutes.

In some cases, the at least 10 CV comprises from 10 to 20 CV. In some cases, the at least 20 CV comprises from 20 to 30 CV.

In some embodiments, the sample separation process comprises: (i) introducing three blank samples into the liquid chromatography system, followed by four reference standard samples, followed by two blank samples, followed by from 1 to 10 test samples, followed by a reference standard sample, followed by a blank sample; and (ii) running the separation gradient of mobile phase A, mobile phase B and mobile phase C through the liquid chromatography system for each sample, respectively.

In some embodiments, the separation gradient is run at a flow rate of 0.8 mL/min for 36 minutes.

In some embodiments, the separation gradient comprises, in sequence: (i) 90% mobile phase A and 10% mobile phase B for 1 minute; (ii) reducing mobile phase A from 90% to 58%, and increasing mobile phase B from 10% to 42% over a period of 20 minutes; (iii) 100% mobile phase C for 4 minutes; and (iv) 90% mobile phase A and 10% mobile phase B for at least 10 minutes.

In some embodiments, the method further comprises diluting the one or more test samples in a dilution buffer from 1.5 to 3 fold (e.g., 2.3 fold) if the test sample comprises $5 \times 10^{12}$ viral genomes/mL (vg/mL).

In some embodiments (e.g., if the test sample contains $5 \times 10^{12}$ vg/mL), each of the one or more test samples introduced into the liquid chromatography system comprises about 10 microliters. In some embodiments (e.g., if the test sample contains $<5 \times 10^{12}$ vg/mL), each of the one or more test samples introduced into the liquid chromatography system comprises about 20 microliters.

In some embodiments, the mobile phase A comprises 20 mM±2 mM bis-tris-propane, and 2 mM±0.2 mM magnesium chloride in purified water at a pH of 8.5±0.1.

In some embodiments, the mobile phase B comprises 20 mM±2 mM bis-tris-propane, 500 mM±50 mM TMAC, and 2 mM±0.2 mM magnesium chloride in purified water at a pH of 8.5±0.1.

In some embodiments, the mobile phase C comprises 2 M±0.2 M sodium chloride in purified water.

In any of the various embodiments, the AAV particles are of serotype AAV1, AAV2, AAV3, AAV4, AAV5, AAV6, AAV7, AAV8, AAV9, AAV-DJ, AAV-DJ/8, AAV-Rh10, AAV-retro, AAV-PHP.B, AAV8-PHP.eB, or AAV-PHP.S. In some cases, the AAV particles are of serotype AAV1, AAV5, or AAV8. In some embodiments, the AAV particles are of serotype AAV8.

In any of the various embodiments of the methods, carry-over from a prior sample run in the liquid chromatography system into a blank sample run is no more than 0.3% of the prior sample full capsid peak. In some cases, the prior sample is a reference standard sample. In some cases, the prior sample is a test sample. In some embodiments, the carry-over is no more than 0.15% of the prior sample full capsid peak.

In various embodiments, any of the features or components of embodiments discussed above or herein may be combined, and such combinations are encompassed within the scope of the present disclosure. Any specific value discussed above or herein may be combined with another related value discussed above or herein to recite a range with the values representing the upper and lower ends of the range, and such ranges are encompassed within the scope of the present disclosure.

Other embodiments will become apparent from a review of the ensuing detailed description.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

As used herein, the terms "include," "includes," and "including," are meant to be non-limiting and are understood to mean "comprise," "comprises," and "comprising," respectively.

Although any methods and materials similar or equivalent to those described herein can be used in the practice or testing of the present invention, the preferred methods and materials are now described. All patents, applications and non-patent publications mentioned in this specification are incorporated herein by reference in their entireties.

Selected Abbreviations

LC: Liquid Chromatography
CV: Column Volume(s)
rAAV: Recombinant AAV Particle or Capsid
AAV: Adeno-Associated Virus
AEX—Anion Exchange Chromatography
GOI—gene of interest Definitions "Intact viral capsid components" refer to viral capsids (e.g., empty viral capsids, partially-full viral capsids, and/or full viral capsids) that are intact (i.e., have not been denatured or otherwise broken down or disintegrated into their component parts (e.g., different viral proteins) and retain the structural characteristics of a viral capsid (e.g., the icosahedral conformation of an AAV capsid).

The terms "empty viral capsids" or "empty capsids" refer to capsids not containing a heterologous nucleic acid molecule (e.g., a therapeutic gene).

The terms "partially-full viral capsids" or "partially full capsids" refer to capsids containing only a portion of a heterologous nucleic acid molecule (e.g., a therapeutic gene).

The terms "full viral capsids" or "full capsids" refer to capsids containing a complete heterologous nucleic acid molecule (e.g., a therapeutic gene or gene of interest).

The term "sample," as used herein, refers to a mixture of viral particles (e.g., AAV particles) that comprises at least one viral capsid component (i.e., empty capsids, partially-full capsids, and/or full capsids), that is subjected to manipulation in accordance with the methods of the invention, including, for example, separating and analyzing.

The terms "analysis" or "analyzing," are used interchangeably and refer to any of the various methods of separating, detecting, isolating, purifying and/or characterizing viral particles or component parts of interest (e.g., AAV capsids). Examples include, but are not limited to, liquid chromatography (e.g., AEX).

"Contacting," as used herein, includes bringing together at least two substances in solution or solid phase, for example contacting a stationary phase of a chromatography material with a sample, such as a sample comprising viral particles or viral proteins.

As used herein, the term "liquid chromatography" refers to a process in which a chemical mixture carried by a liquid can be separated into components as a result of differential distribution of the chemical entities as they flow around or over a stationary liquid or solid phase. A non-limiting example of liquid chromatography includes ion-exchange chromatography (e.g., anion-exchange chromatography).

"Adeno-associated virus" or "AAV" is a non-pathogenic parvovirus, with single-stranded DNA, a genome of approximately 4.7 kb, not enveloped and has icosahedric conformation. AAV was first discovered in 1965 as a contaminant of adenovirus preparations. AAV belongs to the *Dependovirus* genus and Parvoviridae family, requiring helper functions from either herpes virus or adenovirus for replication. In the absence of helper virus, AAV can set up latency by integrating into human chromosome 19 at the 19q13.4 location. The AAV genome consists of two open reading frames (ORF), one for each of two AAV genes, Rep and Cap. The AAV DNA ends have a 145-bp inverted terminal repeat (ITR), and the 125 terminal bases are palindromic, leading to a characteristic T-shaped hairpin structure.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the nucleic acid can comprise sugars and phosphate groups (as may typically be found in RNA or DNA), or modified or substituted sugar or phosphate groups.

A "recombinant AAV particle" refers to an adeno-associated viral particle including one or more heterologous sequences (e.g., nucleic acid sequence not of AAV origin) that may be flanked by at least one, for example, two, AAV inverted terminal repeat sequences (ITRs). Such rAAV particles can be replicated and packaged when present in a host cell that has been infected with a suitable helper virus (or that is expressing suitable helper functions) and that is expressing AAV rep and cap gene products (i.e., AAV Rep and Cap proteins).

A "viral particle" refers to a viral particle composed of at least one viral capsid protein and an encapsulated viral genome.

"Heterologous" means derived from a genotypically distinct entity from that of the rest of the entity to which it is compared or into which it is introduced or incorporated. For example, a nucleic acid introduced by genetic engineering techniques into a different cell type is a heterologous nucleic acid (and, when expressed, can encode a heterologous polypeptide). Similarly, a cellular sequence (e.g., a gene or portion thereof) that is incorporated into a viral particle is a heterologous nucleotide sequence with respect to the viral particle.

An "inverted terminal repeat" or "ITR" sequence is relatively short sequences found at the termini of viral genomes which are in opposite orientation. An "AAV inverted terminal repeat (ITR)" sequence, is an approximately 145-nucleotide sequence that is present at both termini of a single-stranded AAV genome.

The term "isolated," as used herein, refers to a biological component (such as a nucleic acid, peptide, protein, lipid, viral particle or metabolite) that has been substantially separated, produced apart from, or purified away from other biological components in the cell of the organism in which the component naturally occurs or is transgenically expressed.

A "vector," as used herein, refers to a recombinant plasmid or virus that comprises a nucleic acid to be delivered into a host cell, either in vitro or in vivo.

A "recombinant viral vector" refers to a recombinant polynucleotide vector including one or more heterologous sequences (i.e., nucleic acid sequence not of viral origin).

The term "anion-exchange chromatography" or AEX is intended to include a process that separates substances based on their charges using an ion-exchange resin containing positively charged groups, such as diethyl-aminoethyl groups. In solution, the resin is coated with positively charged counter-ions.

The term "liquid carrying components" of a liquid chromatography instrument, refers to those elements of, e.g., an HPLC or UPLC instrument that carry the sample and mobile phase(s) from the point of injection (whether manually or by autosampler) to the column, and from the column to the detector.

General Description

The present disclosure provides liquid chromatography methods that provide sensitive and quantitative characterization of the viral capsid constituents of a sample of viral particles (e.g., AAV particles). Characterization of the viral capsid constituents of viral particle compositions, such as the viral capsid components of a sample of AAV particles, is necessary to ensure product quality and consistency to maintain safety and efficacy of the compositions.

Recombinant viral vector compositions (e.g., AAV vector compositions) can contain varying levels of empty and full capsid components arising from production. The present methods provide analytical techniques to identify and quantitate ratios of viral capsid components in a sample of viral particles.

Methods for Determining Relative Abundance of Viral Capsids Components

Aspects of the disclosure are directed to methods for determining the relative abundance of intact viral capsid components in a sample of AAV particles comprising a heterologous gene-of-interest. In general, the methods include separation of the AAV capsid components using anion exchange chromatography and a determination of the relative abundance of the empty and full capsid components based on the peak area of the separated components.

In some cases, the method comprises: (a) performing a system regeneration process on a liquid chromatography system comprising a liquid chromatography (LC) instrument and an anion exchange column (AEX column) to reduce or eliminate the percentage of carry-over from reference standard samples or prior test samples into blank samples (e.g., less than 0.15% of the area count of the reference standard full capsid peak) that may impact the accuracy and reproducibility of the analysis of test samples; (b) performing a system equilibration process on the liquid chromatography system to clear the liquid carrying components of the LC instrument and the AEX column of wash materials from the regeneration process; and (c) performing a sample separation process on one or more test samples containing empty and full AAV capsids to determine the relative abundance of each capsid component in the one or more test samples.

In some cases, the method comprises: (a) performing a system regeneration process on a liquid chromatography system comprising a liquid chromatography (LC) instrument and an anion exchange column (AEX column), wherein the system regeneration process comprises: (i) washing the AEX column with at least 10 column volumes (CV) of mobile phase A; (ii) washing the AEX column with at least 10 CV of purified water; (iii) washing the AEX column with at least 20 CV of a wash solution comprising from 15% to 21% v/v ethanol in purified water; and (iv) washing liquid carrying components of the LC instrument with the wash solution at a flow rate of at least 0.5 mL/min for at least 30 minutes, wherein mobile phase A comprises from 15 mM to 25 mM bis-tris-propane, and from 1 mM to 3 mM magnesium chloride in purified water at a pH of from 8 to 9, and wherein the purified water has a resistivity of about 18.2 Mohm·cm at 25° C. and less than 5 ppb total organic carbon; (b) performing a system equilibration process on the liquid chromatography system, comprising purging the wash solution from the liquid carrying components of the LC instrument and the AEX column; (c) performing a sample separation process, wherein the sample separation process comprises: (i) introducing one or more blank samples into the liquid chromatography system, and running a separation gradient of mobile phase A, mobile phase B and mobile phase C through the liquid chromatography system; (ii) introducing one or more reference standard samples into the liquid chromatography system, and running a separation gradient of mobile phase A, mobile phase B and mobile phase C through the liquid chromatography system; and (iii) introducing one or more test samples of the AAV particles into the liquid chromatography system, wherein the one or more test samples comprises intact empty AAV capsids and intact full AAV capsids in a sample solution, and running a separation gradient of mobile phase A, mobile phase B and mobile phase C through the liquid chromatography system to separate the intact empty AAV capsids from the intact full AAV capsids, wherein mobile phase B comprises 15 mM to 25 mM bis-tris-propane, from 250 mM to 1 M tetramethylammonium chloride (TMAC), and from 1 mM to 3 mM magnesium chloride in purified water at a pH of from 8 to 9, and mobile phase C comprises 1.5 M to 2.5 M sodium chloride in purified water; and (d) identifying an amount of the intact empty AAV capsids and an amount of the intact full AAV capsids in each of the one or more test samples to determine the relative abundance of the intact viral capsid components in the sample of AAV particles.

In some cases, the method comprises: (a) performing a system regeneration process on a liquid chromatography system comprising a liquid chromatography (LC) instrument and an anion exchange column (AEX column), wherein the system regeneration process comprises: (i) washing the AEX column with at least 10 column volumes (CV) of mobile phase A; (ii) washing the AEX column with at least 10 CV of purified water; (iii) optionally reversing the orientation of the AEX column to reverse the flow within the AEX column; (iv) washing the AEX column with at least 20 CV of a wash solution comprising from 15% to 21% v/v ethanol in purified water; (v) removing the AEX column from the LC instrument; and (vi) washing liquid carrying components of the LC instrument with the wash solution at a flow rate of at least 0.5 mL/min for at least 30 minutes, wherein mobile phase A comprises from 15 mM to 25 mM bis-tris-propane, and from 1 mM to 3 mM magnesium chloride in purified water at a pH of from 8 to 9, and wherein the purified water has a resistivity of about 18.2 Mohm·cm at 25° C. and less than 5 ppb total organic carbon; (b) performing a system equilibration process on the liquid chromatography system, comprising: (i) reinstalling the AEX column into the LC instrument; and (ii) purging the wash solution from the liquid carrying components of the LC instrument and the AEX column; (c) performing a sample separation process, wherein the sample separation process comprises: (i) introducing one or more blank samples into the liquid chromatography system, and running a separation gradient of mobile phase A, mobile phase B and mobile phase C through the liquid chromatography system; (ii) introducing one or more reference standard samples into the liquid chromatography system, and running a separation gradient of mobile phase A, mobile phase B and mobile phase C through the liquid chromatography system; and (iii) introducing one or more test samples of the AAV particles into the liquid chromatography system, wherein the one or more test samples comprises intact empty AAV capsids and intact full AAV capsids in a sample solution, and running a separation gradient of mobile phase A, mobile phase B and mobile phase C through the liquid chromatography system to separate the intact empty AAV capsids from the intact full AAV capsids, wherein mobile phase B comprises 15 mM to 25 mM bis-tris-propane, from 250 mM to 1 M tetramethylammonium chloride (TMAC), and from 1 mM to 3 mM magnesium chloride in purified water at a pH of from 8 to 9, and mobile phase C comprises 1.5 M to 2.5 M sodium chloride in purified water; and (d) identifying the amount of the intact empty AAV capsids and the intact full AAV capsids in each of the one or more test samples to determine the relative abundance of the intact viral capsid components in the sample of AAV particles.

In various embodiments of the methods (including those with the surfactant concentrations discussed below), the sample solution may contain from 2 mM to 100 mM sodium chloride. In some cases, the sample solution contains from 60 mM to 100 mM sodium chloride.

In various embodiments of the methods (including those with the sodium chloride concentrations discussed above), the sample solution may contain from 0.003% w/v to 0.007% w/v surfactant. In some cases, the sample solution may contain 0.005% w/v±0.001% w/v surfactant. In some embodiments, the surfactant is a poloxamer (e.g., poloxamer 188).

In various embodiments of the methods, the liquid chromatography system may be a high-performance liquid chromatography (HPLC) system or an ultra-performance liquid chromatography (UPLC) system. HPLC and UPLC refer to a form of column chromatography that pumps a sample mixture or analyte in a solvent (known as the mobile phase) at high pressure through a column with chromatographic packing material or a matrix (stationary phase). The sample is carried by a moving carrier gas stream, e.g. helium or nitrogen. Stationary phase columns are comprised of chromatography media or resin which interacts with the mobile phase mixture or analyte. Although manual injection of samples is still possible, typical HPLC/UPLC systems are fully automated and controlled by computer. An injector or autosampler, may be employed, connected to an apparatus to house the column hardware, which is further connected to a detector. Types of HPLC and UPLC are well-known in the art. UPLC typically operates at a higher pressure than HPLC and may employ a column with reduced particle size relative to HPLC. HPLC and UPLC instruments are well known in the art, and will be familiar to the skilled artisan.

In various embodiments of the methods, the mobile phase or mobile phases comprise buffer compositions such as bis-tris propane (BTP), for example. Mobile phase buffer concentrations may be varied. For example, concentrations of about 1 mM to about 100 mM (e.g., 1 to 50 mM) may be used. In various embodiments, the buffer concentration may be 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, 30 mM, 31, mM, 32, mM, 33 mM, 34 mM, 35 mM, 36 mM, 37 mM, 38 mM, 39 mM, 40 mM, 45 mM, 50 mM, 55 mM, 60 mM, 65 mM, 70 mM, 75 mM, 80 mM, 85 mM, 90 mM, 95 mM, or 100 mM. In some cases, the buffer concentration may be from 10 mM to 30 mM, or from 15 mM to 25 mM (e.g., of BTP). In some cases, the buffer concentration may be 20 mM±2 mM (e.g., of BTP). In some cases, the buffer concentration may be about 20 mM (e.g., of BTP).

In various embodiments of the methods, the mobile phase or mobile phases may contain one or more salts, e.g., magnesium chloride, sodium chloride, and/or tetramethylammonium chloride (TMAC). In some embodiments, the salt may be at a concentration of about 0.1 mM to about 5 M, or about 0.2 mM, about 0.3 mM, about 0.4 mM, about 0.5 mM, about 0.6 mM, about 0.7 mM, about 0.8 mM, about 0.9 mM, about 1 mM, about 1.25 mM, about 1.5 mM, about 1.75 mM, about 2 mM, about 2.25 mM, about 2.5 mM, about 2.75 mM, about 3 mM, about 3.25 mM, about 3.5 mM, about 3.75 mM, about 4 mM, about 4.25 mM, about 4.5 mM, about 4.75 mM, about 5 mM, about 6 mM, about 7 mM, about 8 mM, about 9 mM, about 10 mM, about 50 mM, about 100 mM, about 150 mM, about 200 mM, about 250 mM, about 300 mM, about 350 mM, about 400 mM, about 450 mM, about 500 mM, about 550 mM, about 600 mM, about 650 mM, about 700 mM, about 750 mM, about 800 mM, about 850 mM, about 900 mM, about 950 mM, about 1.0 M, about 1.5 M, about 2 M, about 3 M, about 3.5 M, about 4 M, about 4.5 M, or about 5 M. In some cases, the mobile phase (e.g., mobile phase A and mobile phase B) may contain from about 1 mM to about 3 mM $MgCl_2$. In some cases, the mobile phase (e.g., mobile phase A and mobile phase B) may contain from about 1.5 mM to about 2.5 mM $MgCl_2$. In some cases, the mobile phase (e.g., mobile phase A and mobile phase B) may contain about 2 mM $MgCl_2$. In some cases, the mobile phase (e.g., mobile phase C) may contain from about 1 M to about 3 M NaCl. In some cases, the mobile phase (e.g., mobile phase C) may contain from about 1.5 M to about 2.5 M NaCl. In some cases, the mobile phase (e.g., mobile phase C) may contain about 2 M NaCl. In some cases, the mobile phase (e.g., mobile phase B) may contain from about 100 mM to about 900 mM TMAC. In some cases, the mobile phase (e.g., mobile phase B) may contain from about 250 mM to about 750 mM TMAC. In some cases, the mobile phase (e.g., mobile phase B) may contain from about 400 mM to about 600 mM TMAC. In some cases, the mobile phase (e.g., mobile phase B) may contain about 500 mM TMAC.

In various embodiments of the methods, the mobile phase or mobile phases contain the buffers and/or salts in purified water at a pH ranging from about 7.5 to about 9.5. The pH of the mobile phase or mobile phases may be 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, or 9.5. In some cases the pH is from about 8.0 to about 9.0. In some cases the pH is from about 8.3 to about 8.7. In some cases, the pH is about 8.5. The purified water may be Milli-Q water. Milli-Q water is purified water produced from a Milli-Q water purification system (Sigma-Aldrich) that will be familiar to those skilled in the art. Milli-Q water has a resistivity of about 18.2 Mohms·cm at 25° C. and less than about 5 ppb total organic carbon.

The system regeneration process discussed herein includes a wash solution comprising about 18% v/v ethanol in purified water. In various embodiments, the ethanol concentration may be from about 10% v/v to about 26% v/v. In some cases, the ethanol concentration may be from about 15% v/v to about 21% v/v. In some embodiments, the ethanol concentration of the wash solution is about 10%, about 11%, about 12%, about 13%, about 14%, about 15%, about 16%, about 17%, about 18%, about 19%, about 20%, about 21%, about 22%, about 23%, about 24%, about 25%, or about 26% v/v in purified water (e.g., Milli-Q water).

In an embodiment, the system regeneration process discussed herein includes, (i) washing the AEX column with at least 10 column volumes (CV) of mobile phase A; (ii) washing the AEX column with at least 10 CV of purified water; (iii) washing the AEX column with at least 20 CV of a wash solution comprising from 15% to 21% v/v ethanol in purified water; and (iv) washing liquid carrying components of the LC instrument with the wash solution at a flow rate of at least 0.5 mL/min for at least 30 minutes. In another embodiment, the system regeneration process discussed herein includes, (i) washing the AEX column with at least 10 column volumes (CV) of mobile phase A; (ii) washing the AEX column with at least 10 CV of purified water; (iii) optionally reversing the orientation of the AEX column to reverse the flow within the AEX column; (iv) washing the AEX column with at least 20 CV of a wash solution comprising from 15% to 21% v/v ethanol in purified water; (v) removing the AEX column from the LC instrument; and (vi) washing liquid carrying components of the LC instrument with the wash solution at a flow rate of at least 0.5 mL/min for at least 30 minutes. In some cases, reference to at least 10 CV corresponds to from 10 CV to 20 CV. In some cases, reference to at least 10 CV corresponds to 10 CV, 11 CV, 12 CV, 13 CV, 14 CV, 15 CV, 16 CV, 17 CV, 18 CV, 19 CV, 20 CV, 21 CV, 22 CV, 23 CV, 24 CV, 25 CV, 30 CV, 35

CV, or 40 CV. Similarly, reference to at least 20 CV may correspond to from 20 CV to 30 CV in some embodiments. In some cases, reference to at least 20 CV corresponds to 20 CV, 21 CV, 22 CV, 23 CV, 24 CV, 25 CV, 26 CV, 27 CV, 28 CV, 29 CV, 30 CV, 31 CV, 32 CV, 33 CV, 34 CV, 35 CV, 36 CV, 37 CV, 38 CV, 39 CV, or 40 CV. Similarly, reference to a flow rate of at least 0.5 mL/min for at least 30 minutes in connection with the system regeneration process may, in some embodiments, correspond to a flow rate of from 0.5 mL/min to 1 mL/min, or 0.5 mL/min to 0.8 mL/min. In some embodiments, reference to a flow rate of at least 0.5 mL/min for at least 30 minutes refers to a flow rate of 0.5 mL/min, 0.6 mL/min, 0.7 mL/min, 0.8 mL/min, 0.9 mL/min, or 1 mL/min, for a duration of 30 minutes, 31 minutes, 32, minutes, 33 minutes, 34 minutes, 35 minutes, 36 minutes, 37 minutes, 38 minutes, 39 minutes, 40 minutes, 45 minutes, 50 minutes, 55 minutes, or 60 minutes. Similarly, references to a duration of at least 10 minutes refer to, e.g., 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, or 29 minutes.

In various embodiments, performing the system regeneration process results in a reduction or elimination of carry-over of capsid components from prior samples (e.g., reference standard samples or prior test samples) into blank samples. In some cases, the blank samples contain less than 0.3% of the area count of the reference standard full capsid peak or prior test sample full capsid peak. In some cases, the blank samples contain less than 0.25% of the area count of the reference standard full capsid peak or prior test sample full capsid peak. In some cases, the blank samples contain less than 0.2% of the area count of the reference standard full capsid peak or prior test sample full capsid peak. In some cases, the blank samples contain less than 0.15% of the area count of the reference standard full capsid peak or prior test sample full capsid peak.

The system equilibration process discussed herein is generally designed to remove wash materials (e.g., the ethanol containing wash solution) from the liquid carrying components of the LC instrument and the AEX column, and to prepare the column for sample separation. In some cases, the system equilibration process includes: (i) purging the wash solution from the liquid carrying components of the LC instrument with purified water at a flow rate of at least 0.5 mL/min for at least 30 minutes; (ii) reinstalling (if previously removed) the AEX column in the LC instrument; (iii) washing the AEX column with at least 10 CV of purified water; (iv) washing the AEX column with at least 10 CV of mobile phase A; (v) washing the AEX column with at least 20 CV of mobile phase B; and (vi) washing the AEX column with at least 20 CV of mobile phase A. In some cases, reference to at least 10 CV corresponds to from 10 CV to 20 CV. In some cases, reference to at least 10 CV corresponds to 10 CV, 11 CV, 12 CV, 13 CV, 14 CV, 15 CV, 16 CV, 17 CV, 18 CV, 19 CV, 20 CV, 21 CV, 22 CV, 23 CV, 24 CV, 25 CV, 30 CV, 35 CV, or 40 CV. Similarly, reference to at least 20 CV may correspond to from 20 CV to 30 CV in some embodiments. In some cases, reference to at least 20 CV corresponds to 20 CV, 21 CV, 22 CV, 23 CV, 24 CV, 25 CV, 26 CV, 27 CV, 28 CV, 29 CV, 30 CV, 31 CV, 32 CV, 33 CV, 34 CV, 35 CV, 36 CV, 37 CV, 38 CV, 39 CV, or 40 CV. Similarly, reference to a flow rate of at least 0.5 mL/min for at least 30 minutes in connection with the system equilibration process may, in some embodiments, correspond to a flow rate of from 0.5 mL/min to 1 mL/min, or 0.5 mL/min to 0.8 mL/min. In some embodiments, reference to a flow rate of at least 0.5 mL/min for at least 30 minutes refers to a flow rate of 0.5 mL/min, 0.6 mL/min, 0.7 mL/min, 0.8 mL/min, 0.9 mL/min, or 1 mL/min for a duration of 30 minutes, 31 minutes, 32, minutes, 33 minutes, 34 minutes, 35 minutes, 36 minutes, 37 minutes, 38 minutes, 39 minutes, 40 minutes, 45 minutes, 50 minutes, 55 minutes, or 60 minutes. Similarly, references to a duration of at least 10 minutes refer to, e.g., 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, or 29 minutes In some embodiments, the separation process includes a mobile phase or mobile phases run as a gradient. Gradients of the mobile phases can be used, for example, if two, three or more mobile phases are used. In the gradient, the concentration or percentage of the first mobile phase can decrease while the concentration or percentage of the second mobile phase increases over the course of the chromatography run. In some cases, the concentration of both first and second mobile phases can be decreased, while the concentration or percentage of a third mobile phase increases (e.g., temporarily) during the course of the chromatography run. For example, the percentage of the first mobile phase can decrease from about 100%, about 99%, about 95%, about 90%, about 85%, about 80%, about 75%, about 70%, about 65%, about 60%, about 50%, about 45%, or about 40% to about 0%, about 1%, about 5%, about 10%, about 15%, about 20%, about 25%, about 30%, about 35%, or about 40% during a portion of, or over the course of, the chromatography run. As another example, the percentage of the second mobile phase can increase from about 0%, about 1%, about 5%, about 10%, about 15%, about 20%, about 25%, about 30%, about 35%, or about 40% to about 100%, about 99%, about 95%, about 90%, about 85%, about 80%, about 75%, about 70%, about 65%, about 60%, about 50%, about 45%, or about 40% during a portion of, or over the course of, the same run. As another example, the percentage of the first mobile phase and the second mobile phase can decrease from about 100%, about 99%, about 95%, about 90%, about 85%, about 80%, about 75%, about 70%, about 65%, about 60%, about 50%, about 45%, or about 40% to about 0%, about 1%, about 5%, about 10%, about 15%, about 20%, about 25%, about 30%, about 35%, or about 40% during a portion of, or over the course of, the chromatography run, and the percentage of a third mobile phase can increase from about 0%, about 1%, about 5%, about 10%, about 15%, about 20%, about 25%, about 30%, about 35%, or about 40% to about 100%, about 99%, about 95%, about 90%, about 85%, about 80%, about 75%, about 70%, about 65%, about 60%, about 50%, about 45%, or about 40% during a portion of, or over the course of, the same run. In certain aspects, the proportion of mobile phase A in the chromatography run decrease and then increases over time. In certain aspects, the proportion of mobile phase B in the chromatography run increases, then decreases, then increases again over time. In certain aspects, the proportion of mobile phase C increases and then decreases in the chromatography run over time. Optionally, the concentration or percentage of the first and second mobile phases can return to their starting values at the end of the chromatography run. The percentages can change gradually as a linear gradient or in a non-linear (e.g., stepwise) fashion. For example, the gradient can be multiphasic, for example, biphasic, triphasic, etc.

In some cases, the separation gradient comprises, in sequence: (i) from 85% to 95% mobile phase A and from 5% to 15% mobile phase B for a period of time (e.g., 1-5 minutes); (ii) reducing mobile phase A from 85-95% to 5070%, and increasing mobile phase B from 5-15% to 30-50% over a period of time (e.g., from 10 to 30 minutes); (iii) 100% mobile phase C for a period of time (e.g., from 1 to 15 minutes); and (iv) from 85% to 95% mobile phase A and from 5% to 15% mobile phase B for a period of time (e.g., 5 to 15 minutes). In an embodiment, the separation gradient comprises, in sequence: (i) 90% mobile phase A and 10% mobile phase B for 1 minute; (ii) reducing mobile phase A from 90% to 58%, and increasing mobile phase B from 10% to 42% over a period of 20 minutes; (iii) 100% mobile phase C for 5 minutes; and (iv) 90% mobile phase A and 10% mobile phase B for 10 minutes.

In some exemplary embodiments, the mobile phase or mobile phases can have a flow rate through the liquid chromatography column of about 0.05 mL/min to about 1 mL/min, or about 0.05 mL/min to about 0.08 mL/min. In some cases, the flow rate is about 0.05 mL/min, about 0.06 mL/min, about 0.07 mL/min, about 0.08 mL/min, about 0.09 mL/min, about 0.1 mL/min, about 0.15 mL/min, about 0.2 mL/min, about 0.25 mL/min, about 0.3 mL/min, about 0.35 mL/min, about 0.4 mL/min, about 0.45 mL/min, about 0.5 mL/min, about 0.55 mL/min, about 0.6 mL/min, about 0.65 mL/min, about 0.7 mL/min, about 0.75 mL/min, about 0.8 mL/min, about 0.85 mL/min, about 0.9 mL/min, about 0.95 mL/min, or about 1 mL/min In some cases, the flow rate is about 0.8 mL/min. In some embodiments, the run time for the mobile phase or mobile phases, whether run as a gradient or not, is between about 1 minute and 60 minutes. In other embodiments, the run time for the mobile phase or mobile phases is about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, or about 45 minutes.

In various embodiments, sample injection or introduction into the liquid chromatography system is limited to about 20 µL per sample. In some cases, injection volume is from about 5 µL to about 20 µL. In some cases, the injection volume is about 5 µL, about 6 µL, about 7 µL, about 8 µL, about 9 µL, about 10 µL, about 11 µL, about 12 µL, about 13 µL, about 14 µL, about 15 µL, about 16 µL, about 17 µL, about 18 µL, about 19 µL, or about 20 µL.

Depending on the viral titer in any particular test sample, the sample may be diluted in a sample dilution buffer. In some cases, the sample dilution buffer comprises 10 mM sodium phosphate, and 0.005% w/v poloxamer 188 in purified water at pH 7.3. For example, in cases in which the viral titer is greater than or equal to 5E±12 vg/mL, the test sample may be diluted from 1.5 to 3 fold with the sample dilution buffer prior to injection or introduction into the liquid chromatography system. In some cases, the test sample is diluted 1.5 fold, 1.6 fold, 1.7 fold, 1.8 fold, 1.9 fold, 2 fold, 2.1 fold, 2.2 fold, 2.3 fold, 2.4 fold, 2.5 fold, 2.6 fold, 2.7 fold, 2.8 fold, 2.9 fold, or 3 fold with the sample dilution buffer. In various embodiments, the test sample (whether diluted based on viral titer, or not), may be contained in a sample solution comprising from about 0.001% to about 0.01% w/v of a surfactant. In some cases, the sample solution comprises from 0.004% to 0.006% w/v of a surfactant. In some cases, the sample solution comprises about 0.005% w/v of a surfactant. In various embodiments, the surfactant may be a poloxamer, such as poloxamer 188.

In various embodiments, the test samples (e.g., in a sample solution) injected or introduced into the liquid chromatography system comprise from about 2 mM to about 100 mM sodium chloride. In some cases, the test samples comprise from about 60 mM to about 100 mM. In various embodiments, the test samples comprises about 1.8 mM, about 1.9 mM, about 2 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 mM sodium chloride.

In various embodiments of the methods discussed herein, the liquid chromatography system may be used with fluorescence detection. In some embodiments, wavelengths for excitation and emission are set at 280 nm±20 nm and 350 nm±20 nm, respectively. In some embodiments, the response time for detectors is set at 0.5 seconds. In some embodiments, the response time is set to generate at least 20 data points across a chromatographic peak. In some embodiments, the response time is set between about 0.1 and 1.0 second.

Viral Particles

In certain aspects, the viral particle is an AAV particle and the methods disclosed can be used to determine the relative abundance of viral capsid components in a sample of AAV particles. The AAV particles may be recombinant AAV (rAAV) particles. The rAAV particle includes an AAV vector encoding a heterologous transgene or heterologous nucleic acid molecule.

In certain aspects, the AAV particles include an AAV1 capsid, an AAV2 capsid, an AAV3 capsid, an AAV4 capsid, an AAV5 capsid, an AAV6 capsid, an AAV7 capsid, an AAV8 capsid, an AAVrh8 capsid, an AAV9 capsid, an AAV10 capsid, an AAV11 capsid, an AAV 12 capsid, or a variant thereof. In certain aspects, the AAV particles are of serotype AAV1, AAV2, AAV3, AAV4, AAV5, AAV6, AAV7, AAV8, AAV9, AAV-DJ, AAV-DJ/8, AAV-Rh10, AAV-retro, AAV-PHP.B, AAV8-PHP.eB, or AAV-PHP.S. In some embodiments, the AAV particles are of serotype AAV1, AAV5 or AAV8. In some embodiments, the AAV particles are of serotype AAV8.

In some aspects, the viral particle (e.g., AAV particle) contains a heterologous nucleic acid molecule (e.g., a therapeutic gene or gene of interest). In some aspects, the heterologous nucleic acid molecule is operably linked to a promoter. Exemplary promoters include, but are not limited to, the cytomegalovirus (CMV) immediate early promoter, the RSV LTR, the MoMLV LTR, the phosphoglycerate kinase-1 (PGK) promoter, a simian virus 40 (SV40) promoter and a CK6 promoter, a transthyretin promoter (TTR), a TK promoter, a tetracycline responsive promoter (TRE), an HBV promoter, an hAAT promoter, a LSP promoter, chimeric liver-specific promoters (LSPs), the E2F promoter, the telomerase (hTERT) promoter; the cytomegalovirus enhancer/chicken beta-actin/Rabbit .beta.-globin promoter and the elongation factor 1-alpha promoter (EF1-alpha) promoter. In some aspects, the promoter comprises a human .beta.-glucuronidase promoter or a cytomegalovirus enhancer linked to a chicken .beta.-actin (CBA) promoter.

The promoter can be a constitutive, inducible or repressible promoter. In some aspects, the invention provides a recombinant vector comprising a nucleic acid encoding a heterologous transgene of the present disclosure operably linked to a CBA promoter. In some cases, the native promoter, or fragment thereof, for the transgene will be used. The native promoter can be used when it is desired that expression of the transgene should mimic the native expression. The native promoter may be used when expression of the transgene must be regulated temporally or developmentally, or in a tissue-specific manner, or in response to specific transcriptional stimuli. In a further aspect, other native expression control elements, such as enhancer elements, polyadenylation sites or Kozak consensus sequences may also be used to mimic the native expression.

In various aspects, the viral particles may be obtained by any known production systems, such as mammalian cell AAV production systems (e.g., those based on 293T or HEK293 cells) and insect cell AAV production systems (e.g., those based on sf9 insect cells and/or those using baculoviral helper vectors). The viral particles may be purified from the cell cultures by using well known techniques such as discontinuous cesium chloride density gradients or other processes, such as column-based downstream processes.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Separation and Identification of Relative Abundance of Empty and Full AAV Capsids Samples containing empty AAV8 capsids and full AAV8 capsids (containing a gene-of-interest) were separated by anion-exchange (AEX) chromatography and the relative abundance of the capsid components was determined. The AEX separation was performed using a BIA Separations, CIMac AAV Empty/Full 0.1 mL analytical column, 1.3 μm pore size, 5.2 mm diameter×4.95 mm length (Cat. No. 110.8503-1.3) on ACQUITY UPLC H-Class system (Waters Corporation) equipped with a fluorescence detector. Mobile phase A (MPA) contained 20 mM bis-tris propane and 2 mM MgCl$_2$ in Milli-Q water at pH 8.5, mobile phase B (MPB) contained 20 mM bis-tris propane, 500 mM tetramethylammonium chloride (TMAC), and 2 mM MgCl$_2$ in Milli-Q water at pH 8.5, and mobile phase C (MPC) contained 2 M NaCl in Milli-Q water. The flow rate for AEX was 0.8 mL/min, and the gradient was as shown in Table 1, below.

TABLE 1

| AEX Separation Gradient | |
| --- | --- |
| Time (min) | Salt Concentration (mM) |
| 0 | 50 TMAC |
| 1 | 50 TMAC |
| 21 | 210 TMAC |
| 22 | 2000 NaCl |
| 26 | 2000 NaCl |
| 26.1 | 50 TMAC |
| 36 | 50 TMAC |

Each sample was diluted to 80 mM NaCl with a sample dilution buffer containing 10 mM sodium phosphate, and 0.005% w/v poloxamer 188 in Milli-Q water at pH 7.3, and a volume of 10 microliters was injected into the UPLC system. Data was recorded using a fluorescence detector with excitation (Ex) and emission (Em) wavelengths of 280 nm and 350 nm, respectively.

The separation protocol demonstrated linearity and precision across a range of viral genome loads, as shown in Table 2, below.

TABLE 2

| Method Linearity and Precision | | | | |
| --- | --- | --- | --- | --- |
| vg Load | % Empty | % Partial | % Full | CV* % Full |
| 3.4E+9 | 6.3 ± 0.5 | 9.0 ± 0.5 | 84.7 ± 0.6 | 0.7 |
| 5.7E+9 | 6.1 ± 0.9 | 8.3 ± 0.5 | 85.6 ± 1.1 | 1.3 |
| 1.1E+9 | 6.1 ± 0.4 | 8.3 ± 0.3 | 85.6 ± 0.2 | 0.3 |
| 5.7E+10 | 6.0 ± 0.2 | 9.0 ± 0.2 | 85.0 ± 0.3 | 0.4 |
| 1.1E+11 | 6.1 ± 0.6 | 8.3 ± 0.9 | 85.6 ± 0.4 | 0.5 |
| 1.7E+11 | 6.3 ± 0.4 | 8.5 ± 0.4 | 85.2 ± 0.2 | 0.2 |
| 2.3E+11 | 6.6 ± 0.0 | 7.9 ± 0.5 | 85.5 ± 0.5 | 0.6 |
| 2.8E+11 | 7.3 ± 0.4 | 12.4 ± 1.4 | 80.3 ± 1.4 | 1.8 |

Each sample is an average of three replicate injections
*coefficient of variation Varying parameters were evaluated using this method (individual changes shown in Table 3, below), to confirm that the best separation was achieved with a mobile phase containing TMAC at a pH of 8.5, an initial TMAC concentration of 50 mM, and initial hold of 1 minute, a gradient slope of 8 mM TMAC per minute, a $MgCl_2$ concentration of 2 mM.

TABLE 3

| Method Parameters Evaluated | |
| --- | --- |
| Method Parameter | Parameter Values Tested |
| Mobile Phase pH | 8, 8.5, 9, 10 |
| Initial Salt Concentration | 0, 20, 50 mM |
| Hold Time at Initial Conditions | 1, 3, 5 minutes |
| Gradient Slope | 8 and 10 mM/min. |
| $MgCl_2$ Concentration | 0, 1, 2, 5 mM |
| Mobile Phase Salt Type | NaCl, TMAC |

Injection volumes greater than 20 microliters (e.g., 25 μL and 30 μL) resulted in peak shape deteriorations that resulted in poor separation of the empty and full capsid components (data not shown).

Example 2: Evaluation of Sodium Chloride Concentration in Sample Solution

Method performance was evaluated in a series of test samples using the separation protocol detailed in Example 1, but varying the concentration of sodium chloride in the test sample solution. 1.05E+14 vg/mL of AAV8-GOI sample was diluted to contain 180, 140, 100, 90, 80, 70, 60, 30, 10 and 1.8 mM sodium chloride in the test sample solution. Samples with sodium chloride concentrations ranging from 1.8 mM to 100 mM did not impact methodperformance (area/vg is similar across these samples), but samples containing sodium chloride concentrations greater than 100 mM (140 mM and 180 mM) negatively impacted separation of the sample capsids (an improvement in separation of empty vs full capsids was observed with 100 mM NaCl, relative to 140 mM and 180 mM). Results are shown in Table 4, below.

TABLE 4

| Impact of NaCl Concentration in Sample Solution | | | |
| --- | --- | --- | --- |
| Titer | NaCl Concentration in AEX Sample (mM) | vg Load | Area/vg |
| 1.05E+14 | 180 | 2.1E+12 | 0.00045 |
| 8.17E+13 | 140 | 1.6E+12 | 0.00060 |
| 5.83E+13 | 100 | 1.2E+12 | 0.00080 |
| 5.25E+13 | 90 | 1.1E+12 | 0.00080 |
| 4.67E+13 | 80 | 9.3E+11 | 0.00080 |
| 4.08E+13 | 70 | 8.2E+11 | 0.00081 |
| 3.50E+13 | 60 | 7.0E+11 | 0.00081 |
| 1.75E+13 | 30 | 3.5E+11 | 0.00082 |
| 5.83E+12 | 10 | 1.2E+11 | 0.00082 |
| 1.05E+12 | 1.8 | 2.1E+10 | 0.00083 |

An absence of NaCl negatively impacted separation (data not shown).

Example 3: Evaluation of Surfactant Concentration in Sample Solution

To evaluate whether the presence of surfactant was desirable in the sample solution (i.e., the test sample composition injected into the LC system) 1.05E+14 vg/mL of AAV8-GOI was diluted 50 fold with 10 mM phosphate, 180 mM sodium chloride at pH 7.3 with (0.005% w/v) and without (0.0001% w/v) poloxamer 188. The two samples contained 2.1E+12 vg/mL upon dilution, were incubated for 1 day at 37° C., and diluted to contain 80 mM sodium chloride for AEX chromatography.

Decreasing the poloxamer 188 concentration from 0.005% w/v to 0.0001% w/v resulted in a significant loss of AAV material (>20% loss) recovered via AEX chromatography (data not shown), confirming the desirability of a surfactant in the sample solution.

Example 4: Evaluation of System Regeneration Process on % Carry-Over into Blank Samples The effect of system regeneration was evaluated using the separation protocol detailed in Example 1. A reference standard was diluted 2.3 fold in sample dilution buffer and injected into the UPLC system, followed by a blank injection. The blank area count was 0.35% of the area count of the reference standard full capsid peak. This process was repeated in a second experiment, and the blank area count was 1.33% of the area count of the reference standard full capsid peak.

Following the identification of significant ghost peaks in the blank injections, a system regeneration process comprising: (i) washing the AEX column with at least 10 column volumes (CV) of mobile phase A; (ii) washing the AEX column with at least 10 CV of purified water; (iii) reversing the orientation of the AEX column to reverse the flow within the AEX column; (iv) washing the AEX column with at least 20 CV of a wash solution comprising from 15% to 21% v/v ethanol in purified water; (v) removing the AEX column from the LC instrument; and (vi) washing liquid carrying components of the LC instrument with the wash solution at a flow rate of 0.5 mL/min for 10 minutes, was performed. Following regeneration, the wash solution was purged from the LC instrument and AEX column, and the column was equilibrated with Milli-Q water, mobile phase A and mobile phase B. As before, a reference standard was diluted 2.3 fold in sample dilution buffer and injected into the UPLC system, followed by a blank injection. The blank area count following this second reference standard injection was 0.11% of the area count of the reference standard full capsid peak. This process was repeated in a second experiment, and the blank area count was 0.08% of the area count of the reference standard full capsid peak. As evidenced by this data, the system regeneration process significantly reduced the % carry-over into the blank injections, and the repeatability of the results indicates low variability and a capability to control carry-over using the system regeneration process.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A method for determining relative abundance of intact viral capsid components in a sample of adeno-associated virus (AAV) particles comprising a heterologous nucleic acid molecule, the method comprising:
(a) performing a system regeneration process on a liquid chromatography system comprising a liquid chromatography (LC) instrument and an anion exchange column (AEX column), wherein the system regeneration process comprises: (i) washing the AEX column with at least 10 column volumes (CV) of mobile phase A; (ii) washing the AEX column with at least 10 CV of purified water; (iii) washing the AEX column with at least 20 CV of a wash solution comprising from 15% to 21% v/v ethanol in purified water; and (iv) washing liquid carrying components of the LC instrument with the wash solution at a flow rate of at least 0.5 mL/min for at least 30 minutes,
wherein mobile phase A comprises from 15 mM to 25 mM bis-tris-propane, and from 1 mM to 3 mM magnesium chloride in purified water at a pH of from 8 to 9, and wherein the purified water has a resistivity of about 18.2 Mohm·cm at 25° C. and less than 5 ppb total organic carbon;
(b) performing a system equilibration process on the liquid chromatography system, comprising purging the wash solution from the liquid carrying components of the LC instrument and the AEX column;
(c) performing a sample separation process, wherein the sample separation process comprises: (i) introducing one or more blank samples into the liquid chromatography system, and running a separation gradient of mobile phase A, mobile phase B and mobile phase C through the liquid chromatography system; (ii) introducing one or more reference standard samples into the liquid chromatography system, and running a separation gradient of mobile phase A, mobile phase B and mobile phase C through the liquid chromatography system; and (iii) introducing one or more test samples of the AAV particles into the liquid chromatography system, wherein the one or more test samples comprises intact empty AAV capsids and intact full AAV capsids in a sample solution, and running a separation gradient of mobile phase A, mobile phase B and mobile phase C through the liquid chromatography system to separate the intact empty AAV capsids from the intact full AAV capsids,
wherein mobile phase B comprises 15 mM to 25 mM bis-tris-propane, from 250 mM to 1 M tetramethylammonium chloride (TMAC), and from 1 mM to 3 mM magnesium chloride in purified water at a pH of from 8 to 9, and mobile phase C comprises 1.5 M to 2.5 M sodium chloride in purified water; and
(d) identifying an amount of the intact empty AAV capsids and an amount of the intact full AAV capsids in each of the one or more test samples to determine the relative abundance of the intact viral capsid components in the sample of AAV particles.

2. A method for determining relative abundance of intact viral capsid components in a sample of adeno-associated virus (AAV) particles comprising a heterologous nucleic acid molecule, the method comprising:
(a) performing a system regeneration process on a liquid chromatography system comprising a liquid chromatography (LC) instrument and an anion exchange column (AEX column), wherein the system regeneration process comprises: (i) washing the AEX column with at least 10 column volumes (CV) of mobile phase A; (ii) washing the AEX column with at least 10 CV of purified water; (iii) optionally reversing the orientation of the AEX column to reverse the flow within the AEX column; (iv) washing the AEX column with at least 20 CV of a wash solution comprising from 15% to 21% v/v ethanol in purified water; (v) removing the AEX column from the LC instrument; and (vi) washing liquid carrying components of the LC instrument with the wash solution at a flow rate of at least 0.5 mL/min for at least 30 minutes,
wherein mobile phase A comprises from 15 mM to 25 mM bis-tris-propane, and from 1 mM to 3 mM magnesium chloride in purified water at a pH of from 8 to 9, and wherein the purified water has a resistivity of about 18.2 Mohm·cm at 25° C. and less than 5 ppb total organic carbon;
(b) performing a system equilibration process on the liquid chromatography system, comprising: (i) reinstalling the AEX column into the LC instrument; and (ii) purging the wash solution from the liquid carrying components of the LC instrument and the AEX column;
(c) performing a sample separation process, wherein the sample separation process comprises: (i) introducing one or more blank samples into the liquid chromatography system, and running a separation gradient of mobile phase A, mobile phase B and mobile phase C through the liquid chromatography system; (ii) introducing one or more reference standard samples into the liquid chromatography system, and running a separation gradient of mobile phase A, mobile phase B and mobile phase C through the liquid chromatography system; and (iii) introducing one or more test samples of the AAV particles into the liquid chromatography system, wherein the one or more test samples comprises intact empty AAV capsids and intact full AAV capsids in a sample solution, and running a separation gradient of mobile phase A, mobile phase B and mobile phase C through the liquid chromatography system to separate the intact empty AAV capsids from the intact full AAV capsids, wherein mobile phase B comprises 15 mM to 25 mM bis-tris-propane, from 250 mM to 1 M tetramethylammonium chloride (TMAC), and from 1 mM to 3 mM magnesium chloride in purified water at a pH of from 8 to 9, and mobile phase C comprises 1.5 M to 2.5 M sodium chloride in purified water; and (d) identifying an amount of the intact empty AAV capsids and an amount of the intact full AAV capsids in each of the one or more test samples to determine the relative abundance of the intact viral capsid components in the sample of AAV particles.

3. The method of claim 1, wherein:

(a) the wash solution comprises 18%±1% v/v ethanol in purified water; and/or (b) the sample solution comprises from 1 mM to 100 mM sodium chloride; and/or (c) the sample solution comprises from 60 mM to 100 mM sodium chloride;

and/or (d) the sample solution comprises from 0.003% w/v to 0.007% w/v surfactant;

and/or (e) the sample solution comprises 0.005% w/v±0.001% w/v surfactant; and/or (f) the surfactant is poloxamer 188.

4. The method of claim 1, wherein the system equilibration process comprises: (i) purging the wash solution from the liquid carrying components of the LC instrument and the AEX column with purified water at a flow rate of at least 0.5 mL/min for at least 10 minutes; (ii) washing the AEX column with at least 10 CV of purified water; (iii) washing the AEX column with at least 10 CV of mobile phase A; (iv) washing the AEX column with at least 20 CV of mobile phase B; and (v) washing the AEX column with at least 20 CV of mobile phase A.

5. The method of claim 2, wherein the system equilibration process comprises: (i) purging the wash solution from the liquid carrying components of the LC instrument with purified water at a flow rate of at least 0.5 mL/min for at least 10 minutes; (ii) reinstalling the AEX column in the LC instrument; (iii) washing the AEX column with at least 10 CV of purified water; (iv) washing the AEX column with at least 10 CV of mobile phase A; (v) washing the AEX column with at least 20 CV of mobile phase B; and (vi) washing the AEX column with at least 20 CV of mobile phase A.

6. The method of claim 2, wherein performing the system equilibration process further comprises washing the liquid carrying components of the LC instrument with purified water at a flow rate of at least 0.5 mL/min for at least 10 minutes prior to reinstalling the AEX column into the LC instrument.

7. The method of claim 6, wherein purging the wash solution from the liquid carrying components of the LC instrument with purified water is performed at a flow rate of at least 0.5 mL/min for at least 30 minutes.

8. The method of claim 1, wherein the at least 10 CV comprises from 10 to 20 CV, and/or wherein the at least 20 CV comprises from 20 to 30 CV.

9. The method of claim 1, wherein the sample separation process comprises: (i) introducing three blank samples into the liquid chromatography system, followed by four reference standard samples, followed by two blank samples, followed by from 1 to 10 test samples, followed by a reference standard sample, followed by a blank sample; and (ii) running the separation gradient of mobile phase A, mobile phase B and mobile phase C through the liquid chromatography system for each sample, respectively.

10. The method of claim 1, wherein the separation gradient is run at a flow rate of 0.8 mL/min for 36 minutes.

11. The method of claim 1, wherein the separation gradient comprises, in sequence: (i) 90% mobile phase A and 10% mobile phase B for 1 minute; (ii) reducing mobile phase A from 90% to 58%, and increasing mobile phase B from 10% to 42% over a period of 20 minutes; (iii) 100% mobile phase C for 4 minutes; and (iv) 90% mobile phase A and 10% mobile phase B for at least 10 minutes.

12. The method of claim 1, further comprising diluting the one or more test samples in a dilution buffer from 1.5 to 3 fold if the test sample comprises ≥5×10$^{12}$ viral genomes/mL (vg/mL), and/or wherein each of the one or more test samples introduced into the liquid chromatography system comprises about 10 microliters.

13. The method of claim 1, wherein each of the one or more test samples introduced into the liquid chromatography system comprises about 20 microliters.

14. The method of claim 1, wherein the mobile phase A comprises 20 mM±2 mM bis-tris-propane, and 2 mM±0.2 mM magnesium chloride in purified water at a pH of 8.5±0.1.

15. The method of claim 1, wherein the mobile phase B comprises 20 mM±2 mM bis-tris-propane, 500 mM±50 mM TMAC, and 2 mM±0.2 mM magnesium chloride in purified water at a pH of 8.5±0.1.

16. The method of claim 1, wherein the mobile phase C comprises 2 M±0.2 M sodium chloride in purified water.

17. The method of claim 1, wherein the AAV particles are of serotype AAV1, AAV2, AAV3, AAV4, AAV5, AAV6, AAV7, AAV8, AAV9, AAV-DJ, AAV-DJ/8, AAV-Rh10, AAV-retro, AAV-PHP.B, AAV8-PHP.eB, or AAV-PHP.S.

18. The method of claim 1, wherein carry-over from a prior sample run in the liquid chromatography system into a blank sample run is no more than 0.3% of the prior sample full capsid peak.

19. The method of claim 18, wherein the prior sample is a reference standard sample, or the prior sample is a test sample.

20. The method of claim 18, wherein the carry-over is no more than 0.15% of the prior sample full capsid peak.

* * * * *